(12) United States Patent
Kim et al.

(10) Patent No.: US 7,323,146 B2
(45) Date of Patent: Jan. 29, 2008

(54) AIR PURIFIER

(75) Inventors: Young-Saeng Kim, Incheon (KR); Chan-Jung Park, Suwon (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 779 days.

(21) Appl. No.: 10/634,999

(22) Filed: Aug. 6, 2003

(65) Prior Publication Data

US 2004/0118285 A1 Jun. 24, 2004

(30) Foreign Application Priority Data

Dec. 23, 2002 (KR) .................. 10-2002-0082685

(51) Int. Cl.
*B01J 19/08* (2006.01)
(52) U.S. Cl. .............. 422/186.06; 422/121; 96/66; 96/69; 55/524
(58) Field of Classification Search ............ 422/121, 422/186.04; 96/66, 69; 55/524
See application file for complete search history.

(56) References Cited

U.S. PATENT DOCUMENTS

| | | | |
|---|---|---|---|
| 4,772,297 A | 9/1988 | Anzai | |
| 5,904,896 A * | 5/1999 | High | 422/4 |
| 7,029,520 B2 * | 4/2006 | Park et al. | 96/66 |
| 7,074,260 B2 * | 7/2006 | Lee et al. | 96/108 |

FOREIGN PATENT DOCUMENTS

| JP | 08182541 | 7/1996 | |
|---|---|---|---|
| JP | 2000-084056 A | 3/2000 | |
| JP | 2000-217900 | 8/2000 | |
| JP | 2001-079444 | * | 3/2001 |

OTHER PUBLICATIONS

Lee, Kwang Hwi et al., Korean Patent Abstract Publication No. 1020010113593, Publication Date 20011228, Application No. 1020010072907, Application Date 20011122, Abstract only.
Choi, Ho Gyeong et al., Korean Patent Abstract Publication No. 1020010113604, Publication Date 20011228, Application No. 1020010075032, Application Date 20011129, Abstract only.
European Office Action for corresponding European patent application No. 03256537.6 dated May 10, 2007 (In English) (7 pgs).
Letter (2 pgs) and Amendment to EPO filing (in English) (13 pgs), Jun. 1, 2007.

* cited by examiner

*Primary Examiner*—Kishor Mayekar
(74) *Attorney, Agent, or Firm*—Staas & Halsey LLP

(57) ABSTRACT

An air purifier provides various air purification functions relating to various environmental conditions by increasing a purification function relative to specific contaminants through replacement of a filter based on the environment to be purified. The air purifier includes a main body of a structure allowing air to pass therethrough. A replaceable filter is received into the main body and is replaceable on a basis of the environmental properties of a space to be purified, removing contaminants in the air passing through the main body. Further, the air purifier includes a dust collecting unit to charge dust particles electrically and to collect the dust particles by electrostatic attraction. In addition, a metal filter functions to collect the dust particles charged in the dust collecting unit, and a HEPA filter is used to collect micro-contaminants. The metal filter is positioned in front of the HEPA filter.

13 Claims, 5 Drawing Sheets

AIR PURIFIER

CROSS-REFERENCE TO RELATED APPLICATIONS

This application claims the benefit of Korean Application No. 2002-82685, filed Dec. 23, 2002, in the Korean Intellectual Property Office, the disclosure of which is incorporated herein by reference.

BACKGROUND OF THE INVENTION

1. Field of the Invention

The present invention relates, in general, to air purifiers and, more particularly, to an air purifier for use in providing clean air by removing dust, bacteria and contaminants in air.

2. Description of the Related Art

As is well known to those skilled in the art, an air purifier is used to provide purified clean air after dust, bacteria and contaminants in the air are eliminated. The air purifier is provided with a dust collecting unit to collect dust, etc. In the dust collecting unit, dust particles electrically charged by corona discharge of an ionizer are collected by electrostatic attraction of a electrostatic filter having a polarity opposite to the polarity of the charged dust particles.

FIG. 1 is a side sectional view of a conventional air purifier. As shown in FIG. 1, the conventional air purifier includes a pre-filter 102, an ionizer 104, a electrostatic filter 106 and a final filter 108. The pre-filter 102 acts primarily to filter relatively large dust particles. The ionizer 104 functions to charge the dust particles electrically to bear a positive polarity by corona discharge between a discharge electrode 104b and ground electrodes 104a positioned at both sides of the discharge electrode 104b. The electrostatic filter 106 has a plurality of horizontal partitions 106a bearing a negative polarity. When the positively charged dust particles flow between the horizontal partitions 106a of the electrostatic filter 106, the dust particles are adsorbed and collected on the negatively charged horizontal partitions by electrostatic attraction. The final filter 108 functions to filter fine dust or bacteria not filtered by the electrostatic filter 106.

However, the conventional air purifier which filters dust, bacteria and contaminants suffers from exhibiting no functions of deodorization, sterilization and removal of hazardous components such as VOCs (volatile organic compounds). Particularly, bacteria may be filtered by the final filter 108, but the air is not completely sterilized. Hence, worry over propagation of the bacteria in the final filter 108 increases. The conventional air purifier is thus not completely effective due to lack of provision of various air purification functions.

SUMMARY OF THE INVENTION

Accordingly, it is an aspect of the present invention to provide an air purifier with various air purification functions required according to various environmental conditions by enhancing a purification function relative to specific contaminants through replacement of a filter based on environments to be purified.

Additional aspects and advantages of the invention are set forth in part in the description which follows and, in part, will be obvious from the description, or may be learned by practice of the invention.

The foregoing and/or other aspects of the present invention are achieved by providing an air purifier including a main body of a structure allowing air to pass therethrough. A functional filter is placed into the main body of the air purifier and is replaceable on a basis of environmental properties of a space to be purified, and thus functions to remove contaminants in the air passing through the main body.

The foregoing/or and other aspects of the present invention are achieved by providing an air purifier including a dust collecting unit to electrically charge dust particles and to collect the dust particles by electrostatic attraction. In addition, a metal filter is used to collect the dust particles charged in the dust collecting unit, and a HEPA filter is used to collect micro-contaminants. The metal filter is generally positioned in front of the HEPA filter.

BRIEF DESCRIPTION OF THE DRAWINGS

These and/or other aspects and advantages of the invention will become apparent and more readily appreciated from the following description of the preferred embodiments, taken in conjunction with the accompanying drawings of which.

DETAILED DESCRIPTION OF THE PREFERRED EMBODIMENTS

Figure 1:
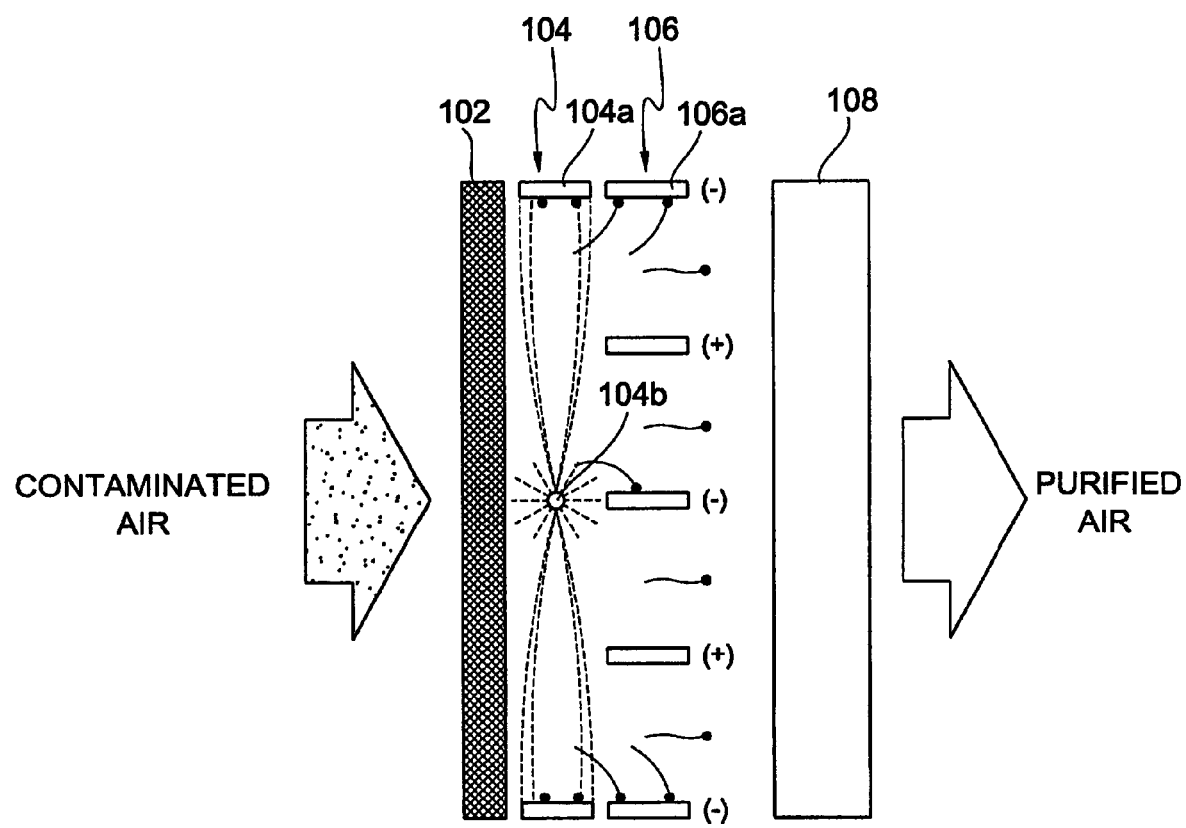
FIG. 1 is a side sectional view of a conventional air purifier.

Reference will now be made in detail to the present preferred embodiments of the present invention, examples of which are illustrated in the accompanying drawings, wherein like reference numerals refer to the like elements throughout. The embodiments are described below in order to explain the present invention by referring to the figures.

Figure 2:
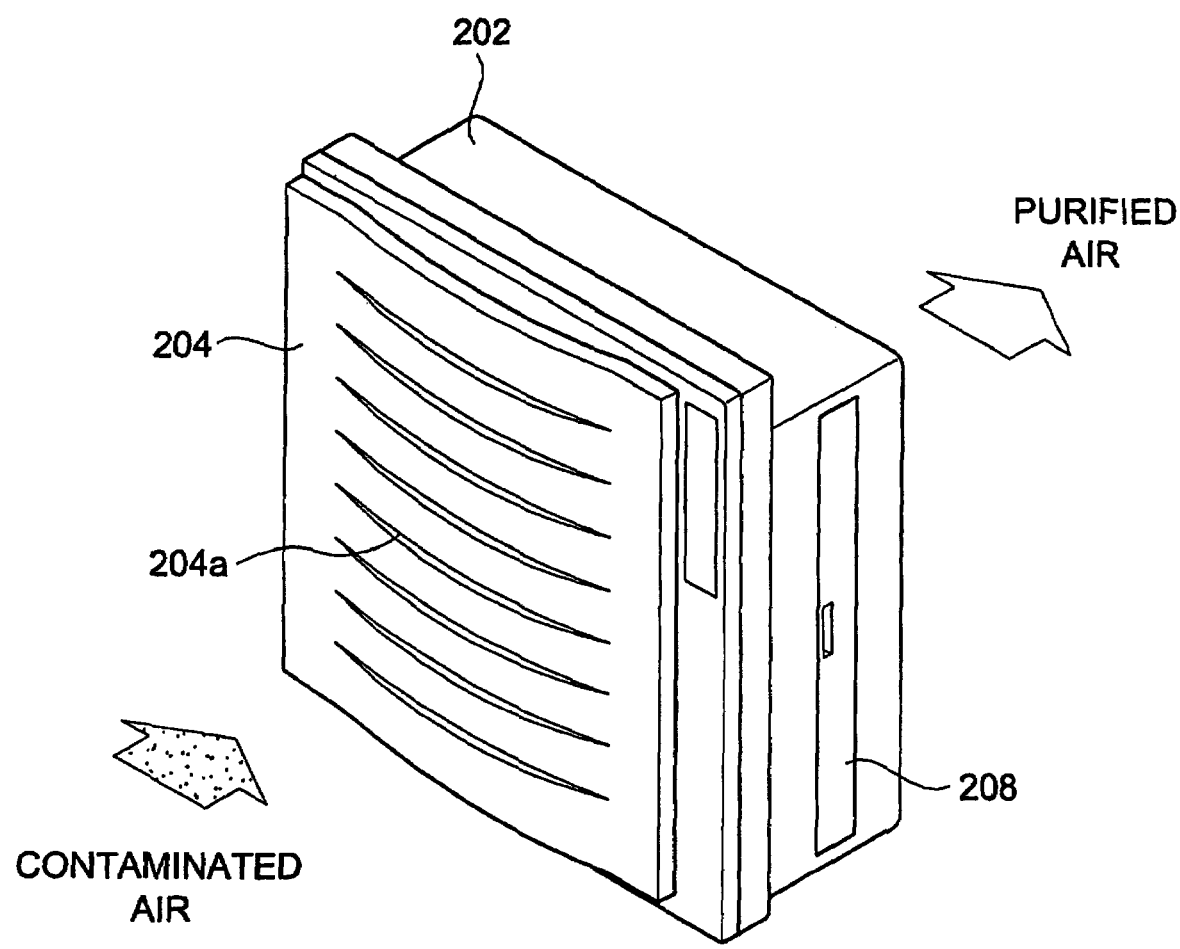
FIG. 2 is a perspective view of an air purifier, according to an embodiment of the present invention.

Embodiments of an air purifier according to the present invention are described in detail with reference to FIGS. 2 to 5. FIG. 2 is a perspective view of an air purifier, according to the present invention. As shown in FIG. 2, a main body 202 of the air purifier is equipped with a cover 204 at a front surface thereof, in which the cover 204 is formed with a plurality of air suction slits 204a so that external air is sucked into the main body 202. That is, through the air suction slits 204a, contaminated air is sucked into the main body 202, which functions to remove dust particles, hazardous components and offensive odors, thus purifying the contaminated air. The purified air is discharged outside the air purifier through an air exhaust port (not shown) positioned at a back surface of the main body 202. At a side surface of the main body 202, a filter replacing port 208 is provided to insert or remove a functional filter in accordance with an embodiment of the present invention.

Figure 3:
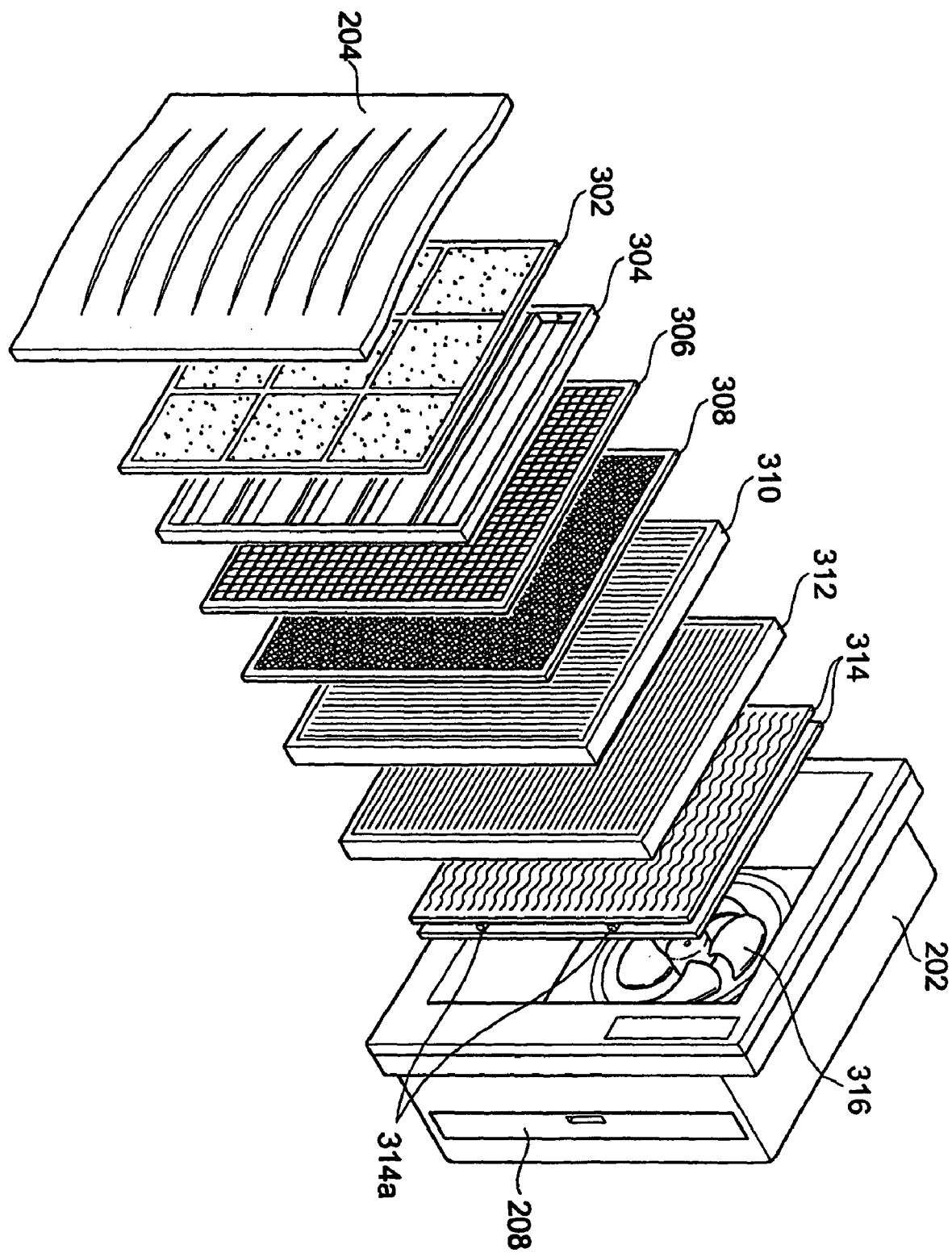
FIG. 3 is an exploded perspective view of the air purifier shown in FIG. 2.

The air purifier is provided with various constituent units necessary for air purification, in addition to the functional filter as mentioned above. FIG. 3 is an exploded perspective view of the air purifier according to an embodiment of the present invention. As shown in FIG. 3, the air purifier according to the present invention includes a pre-filter 302, an ionizer 304, a electrostatic filter 306, a metal filter 308, a HEPA (High-Efficiency Particulate Air) filter 310, a functional filter 312 and photo catalytic filters 314, sequentially disposed from the front to the back of the main body 202 thereof. Further, a fan 316 is equipped at the very rear of the main body 202 to forcibly circulate air from the front to the back of the main body 202. While the fan 316 is rotated, air flows from the front to the back of the main body 202, so that room air is circulated through the air purifier.

Each filter and dust collecting unit shown in FIG. 3 functions as follows. The pre-filter 302 is used primarily to filter relatively large dust particles. The ionizer 304 and the electrostatic filter 306 serve as an electric dust collecting unit, in which dust particles being positively charged in the ionizer 304 are adsorbed and collected to the negatively charged electrostatic filter 306 by electrostatic attraction. The dust particles remaining in the air after passing through the electrostatic filter 306 are filtered through the metal filter 308. The metal filter 308 includes two metal nets having very fine meshes and a plurality of fabric materials interposed between the metal nets, and is electrically grounded to have a negative polarity as in the electrostatic filter 306, thus adsorbing the positively charged dust particles. In the air purifier according to the present invention, dust particles or contaminants, which are not collected in the electrostatic filter 306, are further filtered by the metal filter 308, thus increasing air purification performance, decreasing a filtering burden of the HEPA filter 310 positioned behind the metal filter 308, and lengthening a service life of the HEPA filter 310. Since the HEPA filter 310 is much more expensive than the other filters, extension of service life of the HEPA filter 310 results in a high quality end product, thus generating economic benefits. Moreover, when being made of a washable material, such as a metal or polypropylene, the pre-filter 302, the ionizer 304, the electrostatic filter 306 and the metal filter 308 are semipermanently used, thus further extending the service life of the HEPA filter 310.

The HEPA filter 310 is used to collect microparticulates such as fine dust or bacteria having a very small particle size, i.e., generally has a minimum efficiency of approximately 99.97% for aerosolized DOP (di-octyl-phthalate) (e.g., about 0.3 μm). Compared to the other filters, it is difficult to prepare the HEPA filter 310 with a microstructure necessary for filtering the microparticulates, thus increasing a preparation cost thereof. On the other hand, based on a kind of contaminant to be removed, the functional filter 312 disposed behind the HEPA filter 310 may be replaced with, at any time, a filter having an ability to remove the desired contaminants. The functional filter 312 may function to deodorize, sterilize and/or treat VOCs. In addition, any filter having various functions needed for air purification may be used, thus increasing air purification efficiency. The photocatalytic filters 314 act as a deodorizing filter which eliminates odors from air through reaction of a chemical material coated on the photocatalytic filters 314 with ultraviolet rays generated from ultraviolet lamps 314a positioned between the filters 314.

Figure 4:
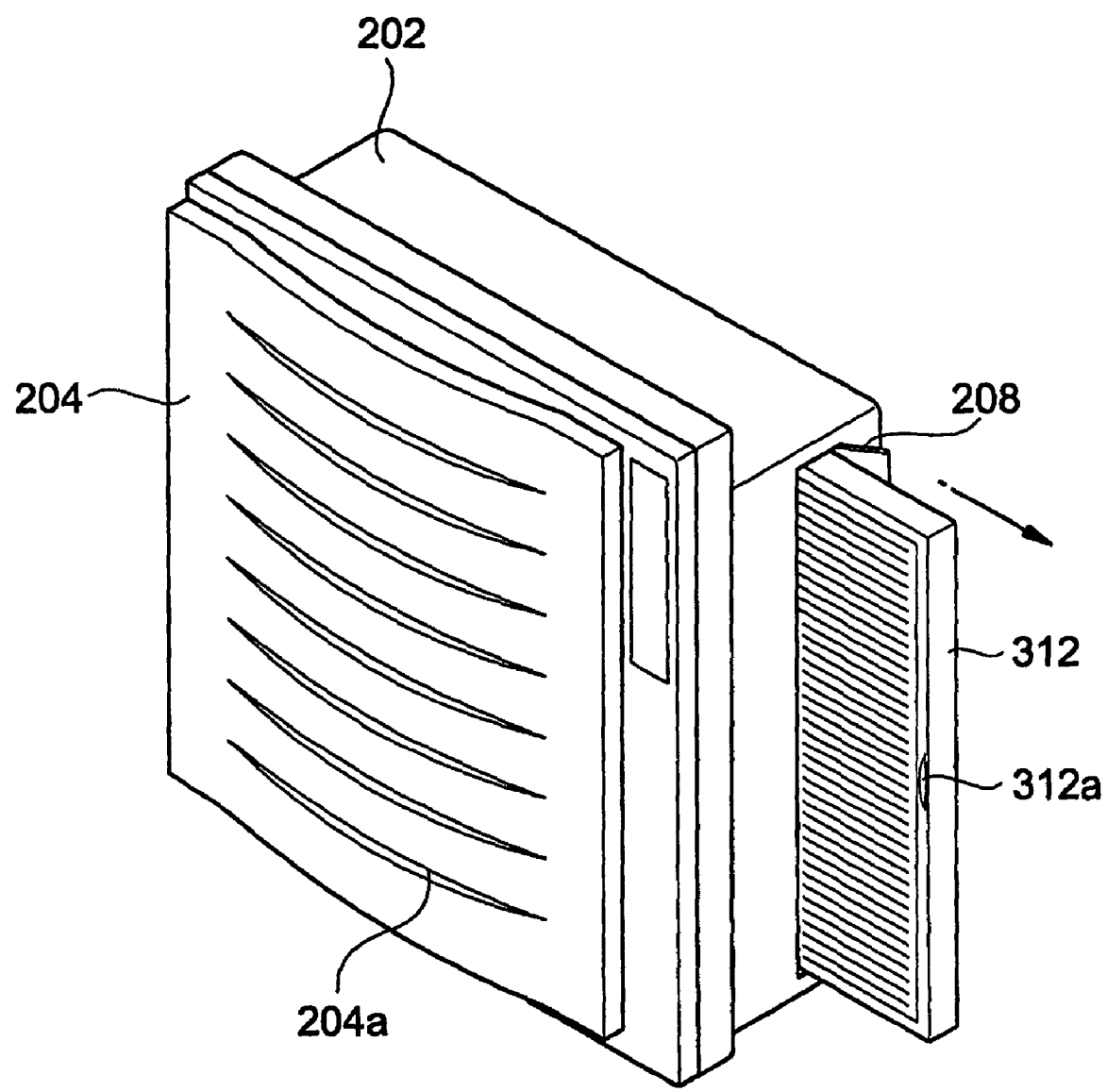
FIG. 4 is a view illustrating a process of removing a functional filter through a filter replacing port of the air purifier shown in FIG. 2.

FIG. 4 is a view illustrating a removal process of the functional filter through the filter replacing port of the air purifier according to the present invention. As shown in FIG. 4, the filter replacing port 208 formed at a side surface of the main body 202 is opened, and the functional filter 312, which has already been disposed in the main body 202, is removed from the main body 202, after which another functional filter is inserted into the main body 202, thus completing replacement of the functional filter 312. One side end of the functional filter 312 is formed with a slot 312a to remove the filter 312 easily from the filter replacing port 208. Through replacement of the functional filter 312, removal efficiencies of the contaminants of the air purifier according to the present invention are further increased. For example, a replaceable deodorizing filter is used in foul-smelling environments, thus exhibiting a deodorization function. In addition, in the case of carpeted indoor spaces, noxious bacteria such as ticks or molds are propagated, and thus, a replaceable sterilizing filter is used to remove the noxious bacteria from the air. Further, various VOCs are contained in the air in regions close to industrial equipment or new buildings. In such a case, a functional filter to remove VOCs is used to increase a removal function of the VOCs.

The functional filter 312 is prepared by incorporating a specific material for air purification into micropores of carbon nanotubes, thus exhibiting various functions of deodorization, sterilization and removal of VOCs. That is, the functional filter 312 according to the present invention has different removing functions based on the functional material confined in the micropores of the carbon nanotubes. For instance, when titanium oxide ($TiO_2$) is confined in the carbon nanotubes, a deodorization function is enhanced. Use of silver (Ag) results in an increased sterilization function, while use of nickel (Ni) leads to increased removal function of VOCs. A seller of the air purifier according to the present invention handles various functional filters having enhanced specific functions, and such filters are basically sold together with the air purifier or may be sold individually.

Figure 5:
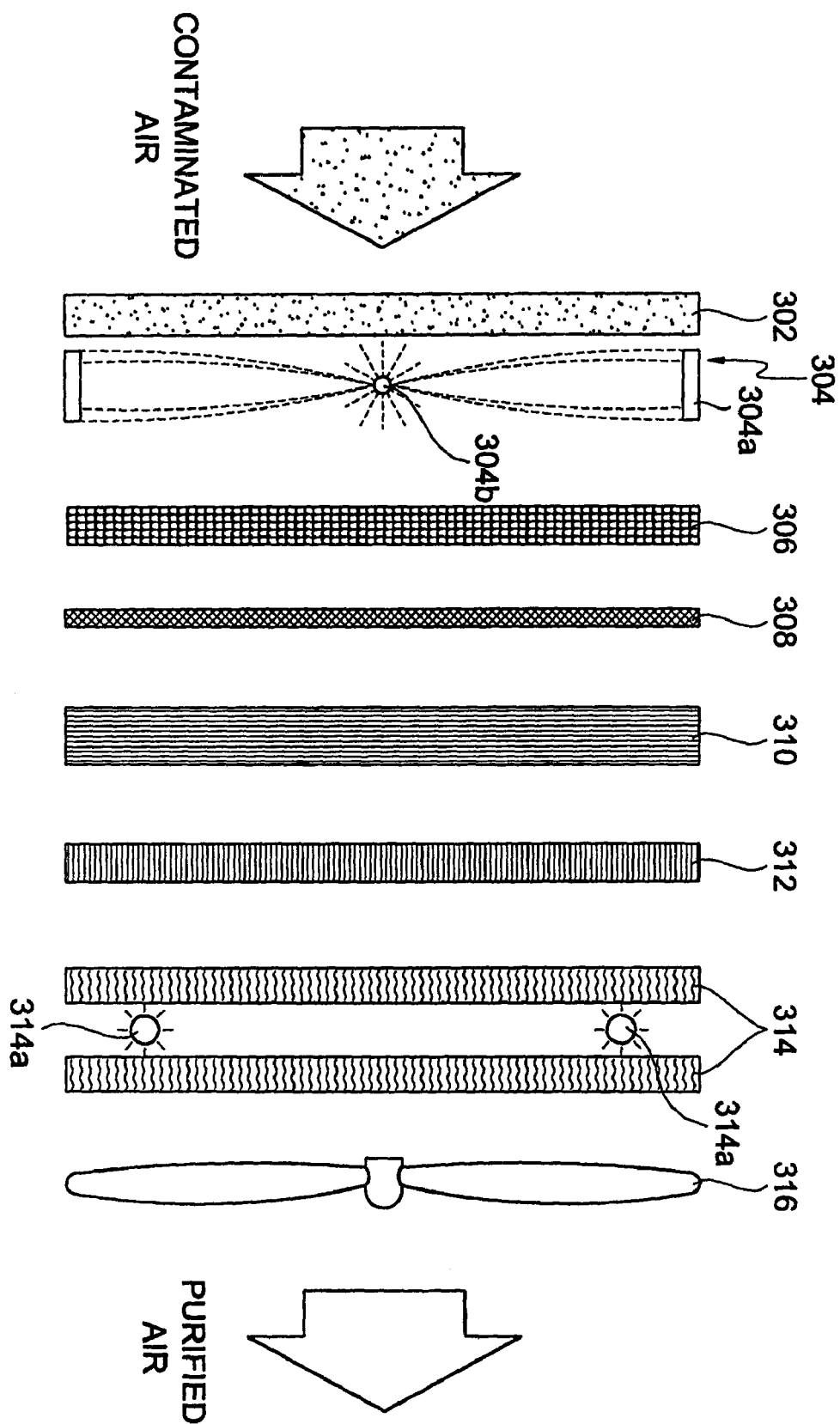
FIG. 5 is a view illustrating functions of the air purifier shown in FIG. 2.

FIG. 5 is a view illustrating functions of the air purifier shown in FIG. 2. As shown in FIG. 5, when contaminated air passes through the pre-filter 302, relatively large dust particles are filtered. By corona discharge between a discharge electrode 304b and ground electrodes 304a, positioned at both sides of the discharge electrode 304b in the ionizer 304, the dust particles are positively charged. The dust particles electrically charged in the ionizer 304 are adsorbed and collected on a surface of the ground electrode 304a. The electrostatic filter 306 has pluralities of partitions 306a having a honeycombed structure, in which the partitions 306a are negatively charged. Thus, the positively charged dust particles are adsorbed and collected on the negatively charged partitions 306a by electrostatic attraction. Fine dust particles remaining in the air after passing through the electrostatic filter 306 are further filtered by the metal filter 308. The HEPA filter 310 collects fine dust particles or molds which are not filtered by the electrostatic filter 306 or the metal filter 308. The functional filter 312, positioned in back of the HEPA filter 310, provides various air purification functions based on a kind of specific materials confined in the micropores of the carbon nanotubes. The photocatalytic filters 314 function to remove odors from the air by reaction of a chemical material coated on the filters 314 with ultraviolet light.

As is apparent from the above description, the present invention provides an air purifier having an enhanced purification function relative to specific contaminants through replacement of a filter on the basis of environmental properties of a space to be purified, thus exhibiting various air purification functions required according to various environmental conditions. That is, by use of a single air purifier, various contaminants are removed, thus increasing purification functions as well as utility of the air purifier. Further, the collection of dust through multi-stages leads to decreasing the filtering burden of the expensive filter, thus lengthening a service life of the air purifier.

Although a few embodiments of the present invention have been shown and described, it would be appreciated by those skilled in the art that changes may be made in this embodiment without departing from the principles and spirit of the invention, the scope of which is defined in the claims and their equivalents.

What is claimed is:

1. An air purifier, comprising:
   a main body to suck and discharge air;
   a dust collecting part to collect dust particles;
   a functional filter to enhance a purification function to predetermined contaminants in the air and to be replaceable by a user in response to the change of contaminants to be purified; and
   a deodorizing filter to remove odors from air,
   wherein the dust collecting part, the functional filter and the deodorizing filter are received into the main body to remove the contaminants from the air sucked into the main body.

2. The air purifier of claim 1, wherein a replacing port of the functional filter to be replaceable on the basis of the types of contaminants to be purified is formed on the main body.

3. The air purifier of claim 2, wherein the replacing port of the functional filter is formed at any one portion of a side surface and a top surface of the main body.

4. The air purifier of claim 1, wherein the dust collecting part comprises a washable material.

5. The air purifier of claim 1, wherein the dust collecting part comprises:
   a pre-filter received into the main body to collect impurities larger than dust particles;
   an ionizer to charge dust particles electrically;
   an electrostatic filter exhibiting static electricity to collect the dust particles charged in the ionizer;
   a metal filter including a fabric material inserted between two metal nets; and
   a high density filter to collect micro-contaminants.

6. The air purifier of claim 5, wherein an electrically charged polarity of the ionizer is opposite to a polarity of the metal filter.

7. The air purifier of claim 5, wherein the fabric material comprising the metal filter is a metal.

8. The air purifier of claim 5, wherein the fabric material comprising the metal filter is polypropylene.

9. The air purifier of claim 5, wherein the high-density filter is a HEPA filter.

10. The air purifier of claim 1, wherein the functional filter comprises a functional material confined in micropores of carbon nanotubes, and has a purification function of contaminants corresponding to the functional material.

11. The air purifier of claim 1, wherein the functional filter comprises nano-sized titanium oxide confined in carbon nanotubes, and functions to remove odors from the air to deodorize the air.

12. The air purifier of claim 1, wherein the functional filter comprises silver confined in micropores of carbon nanotubes, and functions to remove hazardous bacteria in the air to sterilize the air.

13. The air purifier of claim 1, wherein the functional filter comprises nickel confined in micropores of carbon nanotubes, and functions to remove volatile organic compounds.

* * * * *